United States Patent [19]

O'Keeffe

[11] Patent Number: 4,695,555
[45] Date of Patent: Sep. 22, 1987

[54] LIQUID CHROMATOGRAPHIC DETECTOR AND METHOD

[76] Inventor: Andrew F. O'Keeffe, 4801 Deerwood Dr., Raleigh, N.C. 27612

[21] Appl. No.: 924,119

[22] Filed: Oct. 30, 1986

Related U.S. Application Data

[63] Continuation of Ser. No. 743,895, Jun. 12, 1985, abandoned.

[51] Int. Cl.$^4$ .................. G01N 27/00; G01N 30/64
[52] U.S. Cl. .................. 436/150; 210/198.2; 422/68; 422/70; 436/161
[58] Field of Search .......... 210/198.2; 422/55, 56, 422/57, 58, 69, 70, 68; 436/149, 150, 151, 161; 73/61.1 C

[56] References Cited

U.S. PATENT DOCUMENTS

| | | | |
|---|---|---|---|
| 3,322,504 | 5/1967 | Capuano | 436/50 |
| 3,352,643 | 11/1967 | Ando et al. | 23/230 |
| 3,413,842 | 12/1968 | Hecker | 73/61.1 |
| 3,744,296 | 7/1963 | Beltzer | 436/151 |
| 3,775,058 | 11/1973 | Bush | 422/70 |
| 3,896,661 | 7/1975 | Parkhurst et al. | 73/61.1 C |
| 3,902,848 | 9/1975 | Juvet, Jr. et al. | 23/230 R |
| 3,915,642 | 10/1975 | Small et al. | 23/230 R |
| 3,918,906 | 11/1975 | Small et al. | 23/230 R |
| 4,403,147 | 9/1983 | Melera et al. | 250/288 |
| 4,404,065 | 9/1983 | Matson | 436/161 |
| 4,462,962 | 7/1984 | Baba et al. | 422/70 |

OTHER PUBLICATIONS

Sweet, R. G., "High Frequency Recording", Rev. Sci. Inst., 36, 131-36 (1965).
Scott, R. P. W., et al., "Microbore Columns", J. Chromatog., 186, 475-87 (1979).
Mowery, P. A. & Juvet, R. S., "Sensitive Detector", J. Chromat. Sci., 12, 687-95 (1974).
Seymour, R. J. & Boss, C. B., "Droplet Generator", Applied Spectroscopy, 37, 375-59 (1983).
Mason, B. J., et al, "Vibrating Capillary Device", J. Sci. Instrum., 40, 247-49 (1963).
Mason, B. J. & Brownsco, be, J. L., "Uniform Size Drops at Controllable Frequency", J. Sci. Instrum., 41, 258 (1964).
Schneider, J. M. & Hendricks, C. D., "Uniform-Sized Droplets", Rev. Sci. Inst., 35, 1349-50 (1964).
Vonnegut, B. & Neubauer, R. L., "Monodisperse Liquid Particles", J. Colloid Sci., 7, 616-22 (1952).
Berglund, R. N. & Luis, B. Y. H., "Monodisperse Aerosol Standards", Envir. Sci. and Tech., 7, 147,53 (1973).
Liu, B. Y. H. & Pui, D. Y. H. & Chien, Shou-Ming, "Droplet Electrification Detection", Preliminary Report, Aug. 25, 1980, Unpublished.

*Primary Examiner*—Ernest G. Therkorn
*Attorney, Agent, or Firm*—Michael J. Bevilacqua

[57] ABSTRACT

The liquid chromatograph detector of the present invention includes a nozzle communicating with a liquid chromatograph column. A piezoelectric element is firmly affixed to the nozzle and is actuated by an alternating current of a frequency appropriate to cause the firing of charged droplets of a predetermined, uniform size from the nozzle. The emitted droplets pass between two planar deflector plates which are maintained at a DC voltage sufficient to produce a transverse electric field between the plates. The electric field causes droplets passing between the plates to be deflected towards one of the plates and away from the other in a manner and to a degree sensitively dependent upon the charge acquired by the droplet upon discharge from the nozzle. A moving recording medium, such as paper, is positioned to receive the droplets passing between the deflector plates. If necessary, the recording surface is then processed so as to make the impinging droplets visible.

14 Claims, 5 Drawing Figures

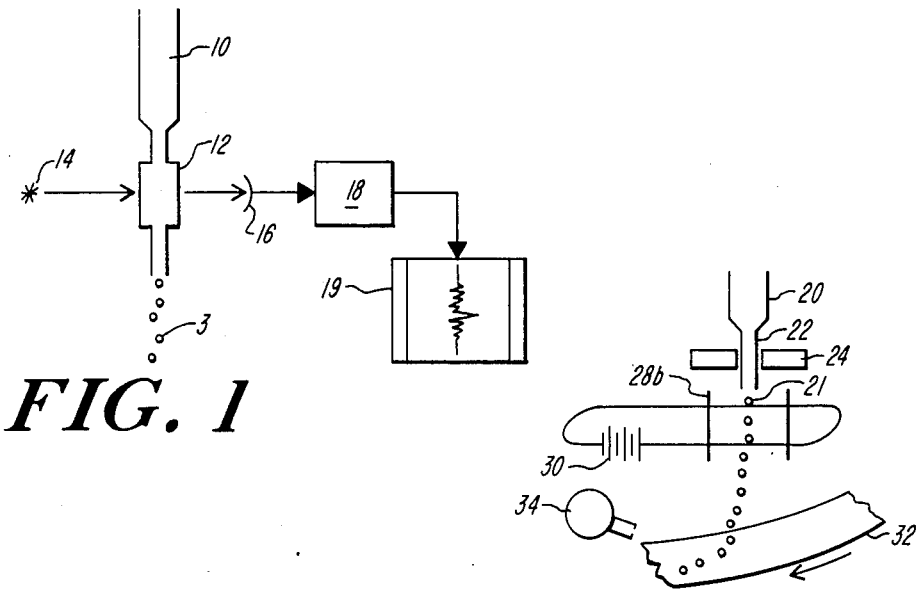
FIG. 1
FIG. 2
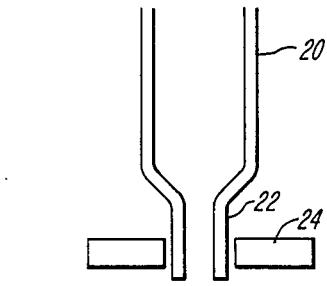
FIG. 3
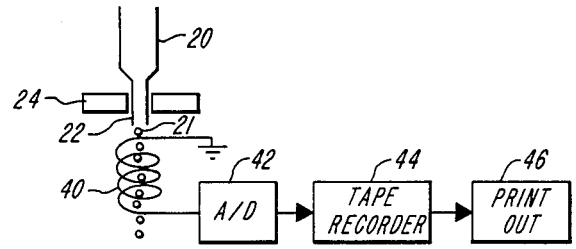
FIG. 4
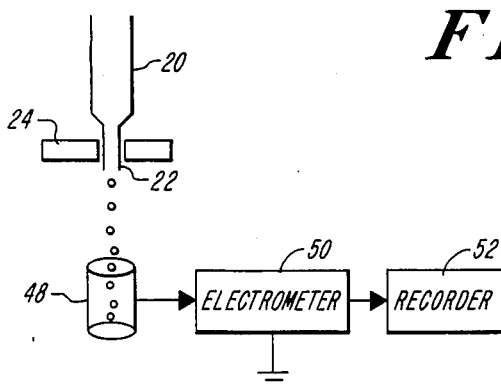
FIG. 5

LIQUID CHROMATOGRAPHIC DETECTOR AND METHOD

This application is a continuation of U.S. Ser. No. 743,895, filed June 12, 1985 now abandoned.

BACKGROUND OF THE INVENTION

This invention relates generally to liquid chromatography, and more particularly to a method and apparatus for detecting the solute burden of the effluent of liquid-chromatograph columns.

A liquid-chromatograph detector generally detects a solute component of a tested effluent with the response of the detector being a measure of the concentration of the particular solute component. Known detectors have been developed to monitor and record, as a function of time, the solute burden of the effluent of liquid chromatograph columns. The majority of these detectors operate on the principle of spectral absorbance of eluate species. Detectors operating on this principle are inherently limited in resolution by the combined effect of two factors: (a) measurement of absorbance demands observation of a finite volume of liquid; and (b) the response time of the photosensor-amplifier-recorder system. The finite volume of liquid is the major component of the extra-column dead volume of a chromatograph in which it occurs, and it imposes a finite limit on the ability of the chromatograph to resolve peaks eluted in rapid succession. It is also evident that a system having a recorder with a response time approaching the interval between two successive eluate peaks can only imperfectly resolve those peaks.

In recent years, detector design has lagged seriously behind column technology. An elegant detector, representative of the best prior art, is that described by Scott et al, 186 *J. Chromatography*, 475-487 (1979). The cell volume of the detector described by Scott et al is stated to be $1.5 \times 10^{-6}$ liters, and its time constant as $40 \times 10^{-3}$ sec. Such a detector, however, would not be adequate to provide the cell volumes and electron time constants commensurate with the separation capability of modern columns.

In known liquid chromatograph detectors, an example of which is shown in FIG. 1, a chromatographic column 10 delivers an effluent liquid to a detector cell 12. Ultraviolet energy from an ultraviolet source 14 passes through cell 12 where portion of the ultraviolet energy is absorbed. The amount of energy absorbed is proportional to the concentration of any chromatographic fraction eluted from the column 10 with that specific increment of effluent then present in cell 12. Remaining energy passes to light sensor 16 which generates an electrical signal amplified by amplifier 18 before being sent on to a strip-chart recorder 19 which produces a graphic record of the chromatographic fraction as a function of time. The usefullness of such detectors is rapidly diminishing in view of the inability of these detectors to handle separation problems demanding smaller cell volumes and time-constants.

It is therefore a pricipal object of the present invention to provide a detection and recording system for liquid chromatographs which displays an improved cell volume.

A further object of the present invention is to provide a detection and recording system displaying an improved time constant.

Still another object of the present invention is to provide a detection and recording system for liquid chromatographs capable of monitoring the most efficient existing liquid chromatograph columns.

Yet another object of the present invention is to provide a detection and recording system for liquid chromatography which is not only valuable in use with microbore columns (herein 30-100 $\mu$m) but can also be used with macro-columns (1 mm or greater) and capillary columns (1-10 $\mu$m).

SUMMARY OF THE INVENTION

The liquid chromatographic detector of the present invention includes a nozzle communicating with a liquid chromatograph column. A piezoelectric element is firmly affixed to the nozzle and is actuated by an alternating current of a frequency appropriate to cause the firing of charged droplets of a predetermined uniform size from the nozzle. The fired charged droplets communicate with a charge detecting means which determines the solute burden of each droplet.

In one embodiment, the emitted droplets pass between two planar deflector plates which are maintained at a DC voltage sufficient to produce a transverse electric field between the plates. This electric field causes droplets passing between the plates to be deflected towards one of the plates and away from the other in a manner and to a degree sensitively dependent upon the charge acquired by the droplet upon emission from the nozzle. A moving recording medium, such as paper, is positioned to receive the droplets passing between the deflector plates. The recording surface is then processed so as to make the impinging droplets visible.

Instead of being passed between two deflector plates, the emitted droplets may be passed through a helical coil in which a charge is induced by the passing charged droplets. In another alternate embodiment, the droplets travel through a radioactive metal cylinder. Air within the cylinder is ionized by the radiation and becomes conductive so that the charge from each droplet is transferred to the cylinder where it is measured.

These and other features and objects of the present invention will become apparent from the following detailed description which should be read in conjunction with the accompanying drawings.

BRIEF DESCRIPTION OF THE DRAWINGS

FIG. 1 is a schematic view of a known liquid chromatograph detector system:

FIG. 2 is a schematic view of the liquid chromatograph detector system of the present invention;

FIG. 3 is an enlarged schematic view of a portion of the liquid chromatograph detector system shown in FIG. 2;

FIG. 4 is a schematic view of an alternate embodiment of the liquid chromatograph detector system shown in FIG. 2;

FIG. 5 is a schematic view of another alternate embodiment of the liquid chromatograph detector system shown in FIG. 2

DETAILED DESCRIPTION OF THE PREFERRED EMBODIMENT

In the liquid chromatographic detector system of the present invention shown in FIG. 2, the exit end of a chromatographic column 20 is closed during fabrication. The closure is pierced with a cylindrical passage having a $20-50 \times 10^{-6}$ m. diameter which forms a nozzle 22 through which droplets 21 are delivered from the column 20. Piezoelectric element 24, firmly affixed to the nozzle 22, is actuated by an alternating current source not shown. (The exit end of the chromatographic column 20, the nozzle 22 and the piezoelectric element 24 are more clearly shown in FIG. 3.) A pair of deflector plates 28a, 28b are arranged on each side of the exit end of nozzle 22 parallel to each other and to the droplet line of flight. A moving recording apparatus including moving paper 32 is positioned adjacent the deflector plates 28a, 28b to receive droplets 21 passing between the plates.

In operation, the effluent liquid is passed through a vibrating orifice of (e.g.) $50 \times 10^{-6}$ m inside diameter emerging therefrom in the form of a directed stream of spherical droplets of uniform size. The droplets 21 are fired from the nozzle 22 at a rate fixed by the frequency of the alternating current actuating the piezoelectric element 24. Each droplet 21 acquires a charge upon propulsion from the nozzle 22 with the charge being dependent upon the solute carried by each droplet. This process which is responsible for the droplets acquiring a charge is commonly known as "waterfall electrification" or "spray electrification". Droplet size is determined by the combined effect of the above-mentioned frequency, the volumetric flow rate of the effluent, the viscosity of the effluent and surface tension. Since each droplet remains isolated from, but in fixed temporal relation to, the preceding and following droplets from the instant of its firing from the vibrating orifice until information has been gathered indicative of its burden of chromatographic fraction (as described below), the cell volume of the chromatographic detector so constituted is precisely the volume of the individual droplet. Since compositional information carried by each droplet is virtually unchanged from the instant of firing until the instant it is recorded, the time constant of the recording system may be seen to be equal to the period of droplet formation which in turn, must be highly uniform, as indicated by the uniformity of droplet size cited above.

The resultant stream of droplets 26 passes between planar deflector plates 28a, 28b maintained by DC source 30 at a voltage sufficient to produce a transverse electrical field of 15 kv/cm therebetween. Each droplet passing between plates 28a, 28b is deflected towards one of the plates 28a, 28b and away from the other, in a manner and to a degree sensitively dependent upon the charge acquired by the droplet upon propulsion from the nozzle 22, this charge in turn being dependent upon the solute(s) carried by each droplet.

Upon emerging from the electric field, each droplet 21 impinges upon the surface of an electrically neutral, relatively non-conducting recording medium (e.g. a band of paper) 32 that is moved at constant velocity in a direction orthogonal to the plane defined by an array of randomly charged droplets passing through the above-described electric field. It will be readily seen that a series of variously charged droplets so impinging will establish on the recording surface a pattern of small droplet-sized charged areas, each positioned in a manner and to a degree dependent upon the charges carried by the impinging droplets. This charge pattern is rendered visible by spraying the paper with xerographic liquid toner from a toner supply 34.

As an alternative to passing the charged droplets fired from the nozzle through the deflector plates 28a, 28b, the droplets 21 can be passed through a helical wire coil 40 as shown in FIG. 4. Each droplet 21 passing through this helical wire coil 40 will induce a charge in the coil. That induced charge is then recorded as a function of time by a recording means such as an electrometer or a sequence of an A/D converter 42, tape recorder 44, and computer display or printout 46.

Instead of passing the charged droplets through the helical coil the droplets could be passed through a metal cylinder 48 containing a radioactive source (e.g. inner surface plated with radioactive cobalt) as shown in the alternate embodiment of FIG. 5. Air within the cylinder 48 is ionized by the radiation and becomes conductive, permitting the charge from each droplet to be transferred to the cylinder where it can be measured and recorded by either an electrometer 50 and recorder 52 or by a sequence of an A/D converter, tape recorder and computer display or printout as used in the embodiment shown in FIG. 4.

The liquid chromatograph detecting system and method disclosed above provide a tremendous improvement in the resolution with which liquid chromatograph eluates can be monitored. The disclosed apparatus allows effective cell volume to be readily reduced to $10^{-10}$ liter with a goal of $10^{-12}$ liter possibly being within reach. It appears that the time constant of the detector system of the present invention will lie within the range of from 1 to $100 \times 10^{-6}$ sec. As will be evident to those skilled in the art, the combination of the above factors will accomplish a gain in resolution approximating their product, i.e. $10^4$ reduction in cell volume times $10^3$ reduction in time constant thereby providing $10^7$ gain in resolution, when compared to the Scott et al detector described above.

While the present invention has been described with reference to its preferred embodiments, it will be understood that modifications and variations will occur to those skilled in the art. Such modifications and variations are intended to fall within the scope of the appended claims.

What is claimed is:

1. An apparatus for detecting the solute burden of an effluent of a liquid chromatograph column comprising:
   means for emitting an effluent liquid stream from the chromatograph column, in the form of spherical droplets, through an opening in the liquid chromatograph column at a constant velocity and over a common path, each of said droplets being imparted with an electric charge due to the spray electrification effect occurring on each droplet as each droplet is emitted from the liquid chromatograph column, the amount of said electric charge acquired by each droplet being dependent upon the nature and quantity of the solute carried by said droplet;
   means for altering the path over which each of said droplets travels as a function of said electric charge acquired by each droplet;
   means for recording the solute burden of each droplet in said series of droplets as a function of the deviation of the droplets from said common path.

2. The apparatus of claim 1 wherein said means for emitting charged spherical droplets comprises:
   piezoelectric element firmly affixed to a nozzle of said liquid chromatograph column through which said droplets are emitted.

3. The apparatus of claim 2 wherein said means for altering the path over which each of said droplets travels comprises:

a pair of deflector plates positioned parallel to said common path of travel of said droplets and parallel to each other;

means for creating a transverse electric field between said pair of parallel deflector plates.

4. The apparatus of claim 1 wherein said means for altering the path over which each of said droplets travels comprises:

deflector means positioned parallel to said common path of travel of said droplets so that said droplets travel through said deflector means;

means for creating a transverse electric field between said deflector means;

said deflector means causing each droplet to be deflected from said common path of travel.

5. An apparatus for detecting the solute burden of an effluent of a liquid chromatograph column comprising:

means for emitting an effluent liquid stream from the chromatograph column in the form of spherical droplets, through an opening in the liquid chromatograph column at a constant velocity and over a common path, each of said droplets being imparted with an electric charge, the amount of said electric charge acquired by each droplet being dependent upon the nature and quantity of the solute carried by said droplet, said means for emitting an effluent liquid stream also including a piezoelectric element firmly affixed to a nozzle of said liquid chromatograph column;

deflector means positioned parallel to said common path of travel of said droplets so that said droplets travel through said deflector means;

means for creating a transverse electric field between said deflector means;

said deflector means causing each droplet to be deflected from said common path of travel;

means for recording the solute burden of each droplet in said series of droplets as a function of the deviation of the droplets from said common path.

6. The apparatus of claim 5 wherein said deflector means comprises:

a pair of deflector plates positioned parallel to said common path of travel of said droplets and parallel to each other.

7. The apparatus of claim 5 wherein said means for recording the solute burden of each droplet comprises:

recording medium positioned for receiving said droplets emitted from said liquid chromatograph column;

means for moving said recording medium to sequentially record individual droplets of said series of droplets.

8. The apparatus of claim 5 wherein said means for recording the solute burden of each droplet comprises:

moving paper means positioned to sequentially receive droplets emitted from said liquid chromatograph column;

means for applying a toner to said moving paper to cause said received droplets to become visible.

9. An apparatus for detecting the solute burden of effluent of a liquid chromatograph column comprising:

means for emitting an effluent liquid stream from the chromatograph column, in the form of spherical droplets, through an opening in the liquid chromatograph column at a constant rate and over a common path, each of said droplets being imparted with an electric charge, the amount of said electric charge acquired by each droplet being dependent upon the nature and quantity of the solute carried by said droplet;

a helical wire coil positioned relative to said nozzle so that each emitted droplet passes through said helical wire coil and induces a charge in said coil;

means for recording the solute burden of each droplet in said series of droplets as a function of said detected electric charge of each droplet.

10. An apparatus for detecting the solute burden of effluent of a liquid chromatograph column comprising:

means for emitting an effluent liquid stream from the chromatograph column, in the form of spherical droplets, through an opening in the liquid chromatograph column at a constant rate and over a common path, each of said droplets being imparted with an electric charge, the amount of said electric charge acquired by each droplet being dependent upon the nature and quantity of the solute carried by said droplet;

a metal cylinder including a radioactive source positioned relative to said emitting means so that said emitted droplets pass through said cylinder, air within said cylinder being ionized by radiation and becoming conductive thereby permitting the charge from each droplet to be transfered to the cylinder;

means for recording the solute burden of each droplet in said series of droplets as a function of said detected electric charge of each droplet.

11. A method of detecting the solute burden of effluent of a liquid chromatograph column comprising the steps of:

emitting an effluent liquid stream, as uniformly sized spherical droplets, through an orifice in the liquid chromatograph column at a constant rate and over a common path, said emitted droplets being imparted with an electric charge, the amount of said electric charge acquired by each droplet being dependent upon the nature and quantity of the solute carried by said droplet:

passing each of said droplets through an electric field which causes each of said droplets to deflect off said common path by a distance dependent on the solute burden in said droplet;

providing an electrically neutral, relatively non conducting recording medium;

positioning said recording medium so that said droplets passing through the electric field will impinge on said recording medium;

processing said recording medium so as to render said impinging droplets visible.

12. The method of detecting the solute burden of effluent of claim 11 further comprising the step of creating an electric field between said two deflector plates which are oppositely charged, said electric field causing each of said droplets to deflect off its common path.

13. The method of detecting the solute burden of claim 11 wherein said step of emitting droplets at a constant rate and over a common path comprises the steps of:

providing a nozzle, communicating with the liquid chromatograph column, through which droplets are emitted;

firmly affixing a piezoelectric element to said nozzle;

actuating said piezoelectric element with an alternating current of a frequency sufficient to provide the proper emission rate.

14. A method of detecting the solute burden of effluent of a liquid chromatograph column comprising the steps of:

emitting an effluent liquid stream, as uniformly sized spherical droplets, through an orifice in the liquid chromatograph column at a constant rate and over a common path, said emitted droplets being imparted with an electric charge due to the spray electrification effect on each droplet occurring as each droplet is emitted from the liquid chromatograph column, the amount of said electric charge acquired by each droplet being dependent upon the nature and quantity of the solute carried by said droplet;

detecting said electric charge of each droplet of said series of droplets by passing said each droplet through a deflector means positioned parallel to said common path of travel of said droplets so that said droplets travel through said deflector means;

creating a transverse electric field within said deflector means for deflecting each droplet from said common path of travel;

recording the solute burden of each droplet in said series of droplets as a function of said detected electric charge of each droplet.

* * * * *